United States Patent
Frelburger et al.

(10) Patent No.: US 6,475,146 B1
(45) Date of Patent: Nov. 5, 2002

(54) METHOD AND SYSTEM FOR USING PERSONAL DIGITAL ASSISTANTS WITH DIAGNOSTIC MEDICAL ULTRASOUND SYSTEMS

(75) Inventors: Paul D. Frelburger, Seattle, WA (US); Sankaralingam Ramraj, San Jose; Aaron J. Schuman, Mountain View, both of CA (US)

(73) Assignee: Siemens Medical Solutions USA, Inc., Iselin, NJ (US)

( * ) Notice: Subject to any disclaimer, the term of this patent is extended or adjusted under 35 U.S.C. 154(b) by 0 days.

(21) Appl. No.: 09/962,383

(22) Filed: Sep. 24, 2001

(51) Int. Cl.$^7$ .................................................. A61B 8/00
(52) U.S. Cl. ...................................................... 600/437
(58) Field of Search ................................ 600/437, 438, 600/443, 447; 342/357.1–357.06; 455/557, 575, 466

(56) References Cited

U.S. PATENT DOCUMENTS

| | | | |
|---|---|---|---|
| 5,957,846 A | 9/1999 | Chiang et al. | 600/447 |
| 5,964,709 A | 10/1999 | Chiang et al. | 600/447 |
| 6,032,120 A | 2/2000 | Rock et al. | 705/2 |
| 6,106,472 A * | 8/2000 | Chiang et al. | 600/447 |
| 6,195,564 B1 * | 2/2001 | Rydbeck et al. | 370/335 |
| 6,252,544 B1 * | 6/2001 | Hoffberg | 342/357.06 |

OTHER PUBLICATIONS

Science Daily Magazine, posted Jul. 11, 2001 "High Tech and High Touch: Wireless Technology Enables Physicians to Access Patient Updates from Anywhere, Anytime", obtained at http://www.sciencedaily.com/releases/2001/07/010711060108.htm, on Jul. 30, 2001, pp. 1–4.

Michael Bartlett, Newsbytes®, posted Aug. 8, 2001, "Doctors Will Learn To Love Handhelds, Eventually—Study", obtained at http://www.newsbytes.com/cgi–bin/udt/im.display.printable?client.id=newsbytes&story.id=168847, Aug. 9, 2001 pp. 1–2.

\* cited by examiner

Primary Examiner—Francis J. Jaworski
Assistant Examiner—Maulin Patel (57) ABSTRACT

An system and method for incorporating the functionality of a personal digital assistant ("PDA") with a diagnostic medical ultrasound imaging system is disclosed. The PDA is capable of controlling the ultrasound system via a wired or wireless communications link. In addition, the personal information management ("PIM") functions of the PDA are integrated together and with the system control functionality to permit automated control and configuration of the ultrasound system based on data stored by the PIM applications.

58 Claims, 2 Drawing Sheets

METHOD AND SYSTEM FOR USING PERSONAL DIGITAL ASSISTANTS WITH DIAGNOSTIC MEDICAL ULTRASOUND SYSTEMS

BACKGROUND

Advances in medical diagnostic technology, and especially in medical diagnostic imaging technologies such as ultrasound, have significantly increased the effectiveness and diagnostic benefits of such technology. However, these advances have also resulted in large ultra-complex devices which are often difficult to physically manipulate and complicated to operate in the clinical setting.

While advances in user interface technologies and miniaturization of electronics have somewhat alleviated these complications, these advances have often facilitated adding even more functionality to new devices rather than simplifying and shrinking existing devices. In the medical environment, this is not necessarily undesirable as clinical space is typically at a premium and the more diagnostic capabilities that can be provided from a single device, the better. Unfortunately, such complexity burdens the clinician who must utilize these devices and technicians who must maintain them.

Further, while increasing the functionality and effectiveness of medical imaging devices, these advances have further significantly reduced the overall operating costs and the related costs to the patient or health insurer. As with any product where cost decreases, supplies and demand have correspondingly increased. This has changed medical imaging from an expensive procedure reserved for those most critically ill to a routine procedure and critical evaluation tool available to benefit any patient for both diagnostic and preventative uses.

This has further resulted in a change in the clinical environment in which such examinations are performed. The past high cost and complexity of such exams dictated that they needed to be performed in a hospital setting by highly trained clinicians or even a radiologist. With the decreasing cost of the medical imaging systems themselves, overall costs now focus on the expense of providing personnel to operate these systems. Commonly, routine medical imaging examinations are performed by nurses or imaging technicians, such as sonographers, or other lower cost personnel. Often the exam is performed and distilled into a report by the nurse or technician and sent to a radiologist for review.

Even the clinical setting of medical imaging has changed. In the past, only hospitals could afford to purchase and operate advanced medical imaging equipment. Today, such systems may be available even in small clinical settings and independent imaging clinics are commonly available for such examinations. In such settings, business considerations, such as efficiency, patient throughput, system utilization and personnel costs become significant concerns. These concerns are paired with the concerns for safe, accurate and complete examination and diagnosis.

Accordingly, there is a need to simplify the use and maintenance of medical diagnostic imaging systems while increasing the functionality of the systems and the effectiveness of the diagnostic examinations performed with them.

SUMMARY

The present invention is defined by the following claims, and nothing in this section should be taken as a limitation on those claims. By way of introduction, the preferred embodiments described below relate to a medical diagnostic imaging system for use with a personal digital assistant. The medical diagnostic imaging system comprises a transmitter, a receiver, a transducer coupled with the transmitter and receiver and a processor coupled with the transmitter and receiver. The processor is operative to control the transmitter and receiver and generate medical diagnostic imaging data representative of the operation thereof. The system further includes a first user interface coupled with the processor and operative to allow a user to perform at least one of a first set of control functions on the imaging system. In addition, the system includes a personal digital assistant ("PDA") interface coupled with the processor and operative to externally couple a PDA with the imaging system. The PDA comprises a second user interface operative to allow a user to perform at least one of a second set of control functions on the imaging system, the PDA interface being further operative to receive input data from the PDA and transmit output data to the PDA.

The preferred embodiments further relate to a method of using a personal digital assistant with a medical diagnostic ultrasound imaging system, the system comprising a processor, a first user interface coupled with the processor and a personal digital assistant ("PDA") interface coupled with the processor. In one embodiment, the method comprises controlling the imaging system and generating medical ultrasound imaging data representative of the operation thereof, performing at least one of a first set of control functions on the imaging system via the first user interface, coupling, externally, a PDA with the imaging system via a personal digital assistant ("PDA") interface coupled with the first user interface and the processor, the PDA comprising a second user interface, performing at least one of a second set of control functions on the imaging system via the second user interface, receiving input data by the PDA interface from the PDA, and transmitting output data by the PDA interface to the PDA.

Further aspects and advantages of the invention are discussed below in conjunction with the preferred embodiments.

DETAILED DESCRIPTION OF THE PRESENTLY PREFERRED EMBODIMENTS

With the initial high cost of diagnostic medical imaging systems, such as ultrasound systems, CT systems and MRI systems, diagnostic medical imaging used to be the exclusive domain of hospitals able to afford the equipment and personnel to operate it. With limited resources, such examinations were relatively rare and typically reserved for the critically ill, resulting in a manageable patient load. As with all technologies, however, more advanced imaging technology is being made available at lower cost and to a wider array of facilities. Such systems are, today, available in a range of clinical settings from small clinics to specialized imaging centers. Now, as with all products where cost decreases, demand increases and new efficiencies need to be considered such as patient scheduling and patient throughput without sacrificing safe and accurate diagnosis.

Figure 1:
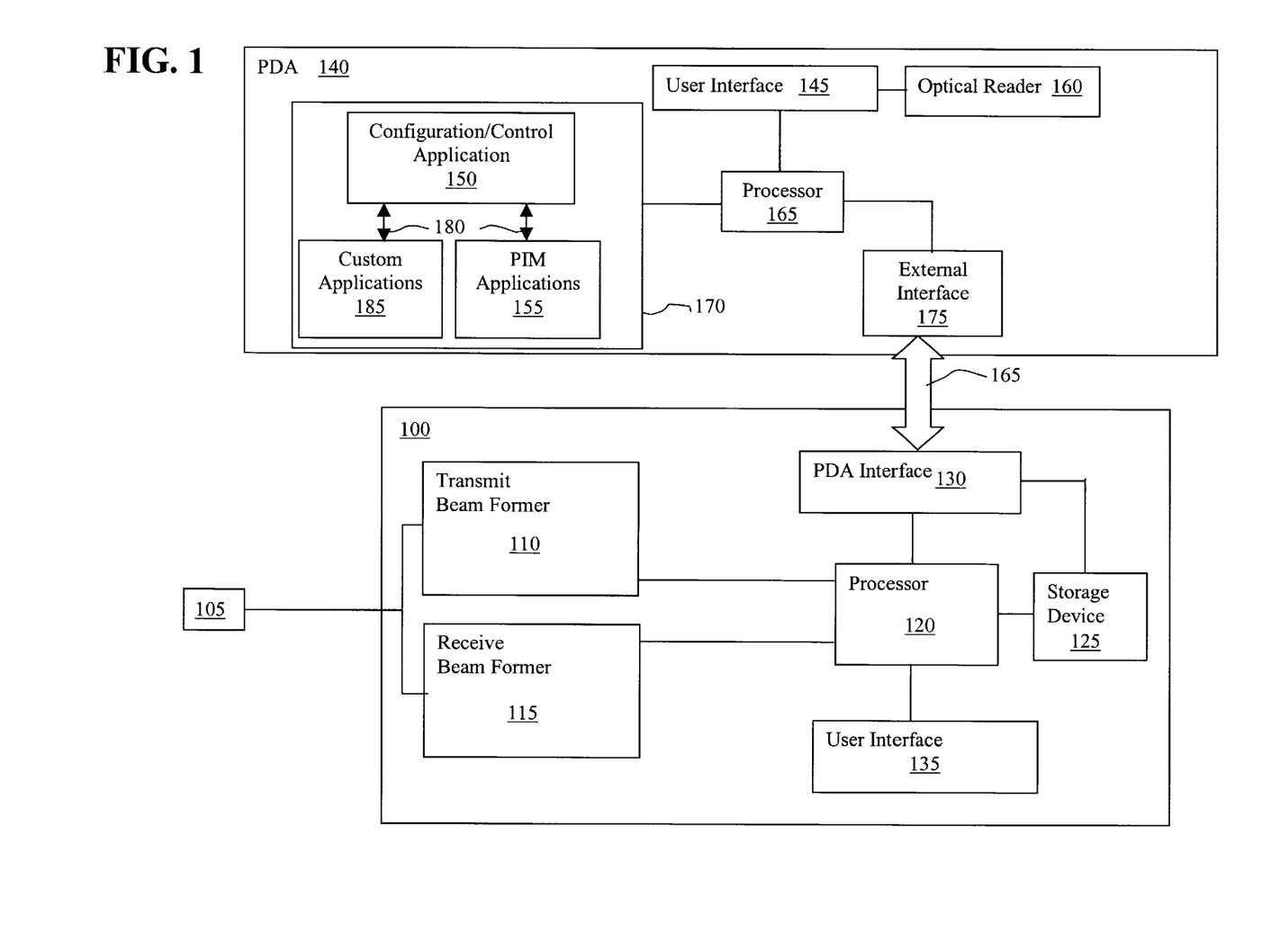
FIG. 1 depicts block diagram of an ultrasound imaging system and personal digital assistant according to one embodiment.

FIG. 1 shows a block diagram of one embodiment of a medical diagnostic ultrasound imaging system 100. It will be appreciated that the disclosed embodiments are applicable to other medical diagnostic imaging systems such as computed radiography, magnetic resonance, angioscopy, color flow Doppler, cystoscopy, diaphanography, echocardiography, fluoresosin angiography, laparoscopy, magnetic resonance angiography, positron emission tomography, single-photon emission computed tomography, x-ray angiography, computed tomography, nuclear medicine, biomagnetic imaging, culposcopy, duplex Doppler, digital microscopy, endoscopy, fundoscopy, laser surface scan, magnetic resonance spectroscopy, radiographic imaging, thermography, radio fluroscopy, or any combination thereof. Further, it will be appreciated that the disclosed embodiments are also applicable to therapeutic ultrasound systems.

As shown in FIG. 1, the ultrasound system 100 comprises a transducer 105 coupled with a transmitter, such as a transmit beamformer 110 and a receiver, such as a receive beamformer 115. Alternatively, as described below, other types of transmitters and/or receivers may be used. Herein, the phrase "coupled with" is defined to mean directly connected to or indirectly connected through one or more intermediate components. Such intermediate components may include both hardware and software based components. The beamformers 110, 115 are each coupled with a processor 120, which is coupled with an optional storage device 125. The term "processor" broadly refers to the appropriate hardware and/or software components of the ultrasound system 100 that can be used to implement the preferred embodiments described herein. It should be understood that any appropriate hardware (analog or digital) or software can be used and that the embodiments described herein can be implemented exclusively with hardware. Further, the processor 120 can be separate from or combined with (in whole or in part) other processors of the ultrasound system 100 (including attendant processors), which are not shown in FIG. 1 for simplicity. It should also be noted that the ultrasound imaging system 100 can comprise additional components. Further, the ultrasound system 100 can be used with any suitable imaging mode (e.g., B-mode imaging, Doppler imaging, tissue harmonic imaging, contrast agent harmonic imaging, etc.), and the transducer 105 can be of any type (e.g., 1D, 1.5D, 2D, plano-concave, single element, phased-array, etc.).

In operation, the processor 120 causes the transmit beamformer 110 to apply a voltage to the transducer 105. The transducer 105 vibrates and emits an ultrasonic beam into an object, such as human tissue (i.e., a patient's body). Ultrasonic energy reflected from the body impinges on the transducer 105, and the resulting voltages created by the transducer 105 are received by the receive beamformer 115. The processor 120 processes the sensed voltages to create an ultrasound image associated with the reflected signals and displays the image on a display device (not shown). The processor 120 can also store the generated image and other ultrasound examination data in the storage device 125 (e.g., a hard drive). As used herein, the term "ultrasound examination data" is meant to broadly refer to ultrasound image data (still images and/or dynamic clips) and/or non-image data (such as calculation data and patient data) associated with an ultrasound examination.

It will be appreciated that alternative methods of generating and controlling ultrasonic energy as well as receiving and interpreting echoes received therefrom for the purpose of diagnostic imaging, now or later developed, may also be used with the disclosed embodiments in addition to or in substitution of current beamforming technologies. Such technologies include technologies which use transmitters and/or receivers which eliminate the need to transmit ultrasonic energy into the subject along focused beam lines, thereby eliminating the need for a transmit beamformer, and may permit beam forming to be performed by post processing the received echoes. Such post-processing may be performed by a receive beamformer or by digital or analog signal processing techniques performed on the received echo data. For example, please refer to U.S. patent application Ser. No. 09/518,972, entitled "METHOD AND APPARATUS FOR FORMING MEDICAL ULTRASOUND IMAGES", now U.S. Pat. No. 6,309,356, and U.S. patent application Ser. No. 09/839,890, entitled "METHOD AND APPARATUS FOR FORMING MEDICAL ULTRASOUND IMAGES", the disclosures of which are herein incorporated by reference.

In the disclosed embodiments, the ultrasound system 100 further comprises a portable computing device or personal digital assistant ("PDA") device interface 130. The PDA interface 130 couples a portable computing device, such as a PDA, with the ultrasound system 100 as will be described below.

The portable computing device/PDA interface 130 can take any suitable form, such as, for example, a wireless communication device, (e.g. an infrared or RF based system), or a cradle or other wired medium, that allows physical and electrical coupling between a portable computing device and the ultrasound system 100. For simplicity, the term "portable computing device" is used herein to broadly refer to any device comprising a processor and storage media that can be used to implement the embodiments described herein. While it is preferred that the portable computing device be a commercially-available, off-the-shelf product, the portable computing device can take the form of a customized device, such as one containing an application-specific processor, a wireless interface, a set of control buttons, and a storage unit (e.g., a Digital 8 microcassette or micro-hard disk drive).

Two examples of a portable computing device are a laptop computer (also known as a notebook computer) and a personal digital assistant (also known as a handheld or palmtop computer). A laptop computer is a full-fledged computer system that has a processor that typically includes a floating point unit (FPU), a communications bus, connection-based network communications, rotating magnetic storage (such as a hard disk or floppy drive), and a video controller chip. The processor may be specifically designed for low power or battery powered operation. A typical laptop is battery operated, weighs less than about five pounds, and has a thickness of less than about three-inches, allowing it to be transported and used in airplanes, libraries, temporary offices, and meetings. Laptop computers generally have the same capabilities as desktop computers and can be effectively turned into a desktop computer with a docking station.

In contrast to a typical laptop computer, a typical personal digital assistant (or "PDA") uses a less complex central processor having more integrated system functionality. The processor of a PDA is typically designed for low power or battery powered operation. Although a PDA contains a data storage device, it typically lacks rotating magnetic storage media. A PDA may also lack an FPU and a video controller, absorbing their functionality into the less-powerful central processor. Unlike laptop computers, PDA's run scaled-down versions of operating systems. For example, instead of using Microsoft's Windows 95/98, some PDA's use Microsoft's Windows CE/Pocket PC, which is a small, scalable operating system that has a similar look-and-feel to Windows 95/98. Also unlike laptop computers which allow the same or virtually the same functionality as a desktop computer, a PDA is typically used merely to organize personal information (e.g., storing names, addresses, and phone numbers and maintaining schedules), enter notes, and perform simple calculations. Other PDA's offer scaled down/pocket-sized versions of word processing and spreadsheet applications. Additionally, while some PDA's (such as the Jomada™ 820 Handheld PC from Hewlett-Packard) look like a laptop computer and use a touch-typeable keyboard, other PDA's (such as Palm Inc.'s Pilot™) are small enough to be stored in a user's pocket and use a stylus, an electronically-sensitive pad, and handwriting recognition software (e.g., Grafitti™).

Many PDA's use wireless technology which operates via the electromagnetic spectrum (e.g., an infrared or RF communications link) to transfer data to/from other computer systems and can also include telephony components to exchange e-mail and faxes, provide paging functions, and retrieve information from the Internet or other network based services. PDA's can also transfer or receive data from another computer system via a wired connection. For example, a PDA can be physically and electrically coupled with a computer via a cradle. In operation, when a user slides the PDA into the cradle, electrical contacts on the PDA physically connect with electrical contracts on the cradle, allowing data transfer or synchronization between the computer and the PDA. Instead of a cradle, a cable can be used to physically and electrically connect the two devices. For devices which use wireless connections, such as infrared or RF based connections, mere proximity, or proximity coupled with user initiation, causes the PDA to negotiate a communications link over the RF or infrared based connection with the computer allowing data transfer or synchronization.

As used herein, a PDA, also referred to as a "handheld computer" or "handheld," is a term for any small mobile, typically capable of being hand-held, device that provides self-contained computing and information storage and retrieval capabilities for personal or business use, often for keeping schedule calendars and address book information handy. Exemplary PDA's include the Palm Pilot™ series manufactured by Palm Computing Inc., located in Santa Clara, Calif. and the Compaq IPAQ™ 36xx series manufactured by Compaq Computer Corporation, located in Houston, Tex. PDA's are generally classified by their operating system, e.g. Palm OS manufactured by Palm Computing, Inc., located in Santa Clara, Calif. and Pocket PC, also known as Windows CE, manufactured by Microsoft Corporation, located in Redmond, Wash. It will be appreciated that other devices with other operating systems or other capabilities, such as wireless networking capabilities, may also be used with the disclosed embodiments.

Most PDA's have a small keyboard or an electronically sensitive pad on which handwriting or other pen-based input can be received. The pad may be combined with the display. Typical uses for PDA's include schedule and address book storage and retrieval and note-entering. However, many other application software programs have been developed for PDA's. Increasingly, PDA's are combined with telephone, paging and other wireless systems.

The disclosed embodiments integrate one or more PDA's with an ultrasound imaging system 100 so as to leverage the functionality and physical size of the PDA to enhance the usability of the ultrasound imaging system 100. In addition to the functionality disclosed below, in one embodiment, the processor 120 is operative to transfer ultrasound examination data from the storage device 125 to the portable computing device/PDA via the PDA interface 130 for the purpose to moving data between ultrasound systems 100 and between an ultrasound system 100 and a reviewing station. For more detail, please refer to commonly assigned U.S. patent application Ser. No. 09/538,320, entitled "MEDICAL DIAGNOSTIC ULTRASOUND IMAGING SYSTEM AND METHOD FOR TRANSFERRING ULTRASOUND DATA TO A PORTABLE COMPUTING DEVICE" filed Mar. 30, 2000, the disclosure of which is herein incorporated by reference. In an alternate embodiment, the PDA is used as an alternate display to display ultrasound image data. For more detail, please refer to U.S. Pat. Nos. 6,106,472, 5,964,709 and 5,957,846, the disclosures of which are herein incorporated by reference.

FIG. 1 shows a PDA 140 coupled with the PDA interface 130 of the ultrasound imaging system 100. The PDA 140 includes a processor 165, memory 170, a user interface 145 and an external interface 175. The processor 165 may be a general purpose CPU such as a Pentium™ class processor or may be a low power/mobile specific processor such as a StrongARM™ processor, both manufactured by Intel Corporation, located in Santa Clara, Calif. Alternatively, the processor 165 may include a custom designed processor. The processor 165 is coupled with the memory 170. The memory 170 includes storage for program and operating program code as well as working storage for device operation. Further, the memory 170 may include both volatile and non-volatile memories. The volatile memory may include dynamic or static RAM or other memory technology. The non-volatile memory may include flash memory or other field or factory re-programmable memory technology or may be a permanent ROM memory. The user interface 145 includes both the hardware and software components necessary to interface with a user of the PDA 140. Some software components may be stored in the memory 170. The user interface 145 includes physical input devices such as a touch sensitive display screen, keyboard, microphone or function buttons. The user interface 145 further includes output devices such as a color, grayscale or black and white display screen, audio speaker/output, vibrating or LED indicators. The software components of the user interface 145 receive user input from, and provide outputs to, the hardware components and generally interface the user with the applications and operating system which are operating on the PDA 140, as will be described below.

The external interface 175 is coupled with the processor 165 and provides connectivity of the PDA 140 to external devices such as to desktop or laptop computers, other PDA's 140, and networks, such as the Internet or intranets/local area networks. Further, the external interface 175 provides connectivity to the imaging system 100 as will be described. The external interface 175 may include one or more of the following types of wired and/or wireless interfaces: infrared, RF based, such as Bluetooth or 802.1 lb, serial, cellular, plain old telephone service ("POTS"), universal serial bus, IEEE 1394 (Firewire™), Ethernet or combinations thereof including interface technologies now or later developed such as satellite based technologies. The external interface 175 may be controlled by the processor 165 and/or software stored in the memory 170. In an alternative embodiment, the external interface 175 operates independently of the processor 165.

The external interface 175 facilitates communications between the PDA 140 and the external device to which the PDA 140 is connected to. In one application, the external interface 175 facilitates synchronization of data and/or application software stored in the memory 170 of the PDA 140 with the external device. In another application, the external interface 175 facilitates information or data transfer to or from the external device such as for the purpose of transmitting or receiving messages such as electronic mails. In yet another application, the external interface 175 facilitates telephony services such as cellular communication, facsimile transmission and POTS access.

In alternative embodiments, the PDA 140 may further support optional devices via optional interfaces such as optional storage and communications devices. Such devices may include devices complying with the PC card, Compact Flash card, Secure Digital Media card, or Smart Media card standards such as flash memory storage devices, POTS or cellular modems, wireless or wired networking devices, and hard disk drives such as the IBM Micro-drive™. Further, optional devices may further include printers or external display drivers capable of driving external display devices such as overhead projectors or CRT or LCD based monitors. Other optional devices may include input devices such as keyboards, microphones or bar code readers, as will be described below.

The memory 170 of the PDA 140 also stores the software applications for use with the PDA 140. In alternate embodiments, these applications may be stored in alternate storage such as a flash memory card or hard disk drive. Typically, PDA's 140 come pre-configured with personal information management ("PIM") software. PIM software typically includes such applications as a calendar/scheduling application, a contacts manager application, an email application, a task manager application and a notes/word processing application. These applications are often designed as lesser functional counterparts which synchronize, via the external interface 175, to fully functional PIM applications which run on fill featured desktop or laptop computers. The disclosed embodiments leverage the functionality of these PIM software applications to enhance the functionality of the imaging system 100, as will be described. PDA's 140 may also utilize custom software applications, either proprietary or publicly available.

As was described, the PDA 140 provides for different methods of inputting data and commands such as a keyboard, touch sensitive display screen or audio input. For example, the touch sensitive display screen may be used to allow handwritten input which may then be automatically converted into computer readable data. In addition, the PDA 140 may provide an optical reader 160, such as a bar code reader, which is capable of scanning and inputting data from a data source that is visually represented, i.e. represented in the visible portion of the electromagnetic spectrum, such as by a bar code, on a medium, such as paper, plastic or metal. It will be appreciated that the optical reader 160 may be coupled directly with the ultrasound system 100 to perform the disclosed functions which utilize the reader 160.

A bar code (or barcode) is the small visible image of lines (bars) and spaces that is affixed, i.e. printed or displayed, to a medium, such as paper, plastic, metal or displayed on a computer display, which represents a piece of data. The code uses a sequence of vertical bars and spaces to represent numbers and other symbols or codes. As used herein, the term barcode also refers to other visual representations which may be used to achieve one or two dimensional and other types of visual data representations. Further, the visual representations may be alphanumeric representations, human readable or not, and the optical reader may further include an optical character recognizer component to convert the alphanumeric representations to computer readable data. An optical reader 160, such as a bar code reader, is used to read the code. The reader uses a laser beam or other appropriate light source, that is sensitive to the reflections from the line and space thickness and variation. The reader translates the reflected light into digital data that is transferred to a computer for immediate action or storage. It will be appreciated that data/code may be encoded using another portion of the electromagnetic spectrum such as the ultraviolet region, allowing such bar codes to be concealed from human-visual detection.

FIG. 1 further shows a PDA 140 configured with PIM software applications 155, described above, and an ultrasound configuration/control application 150. Other application software may also be loaded in the memory 170 of the PDA 140. The configuration/control application 150 is coupled with the PIM software applications 155 via an application program interface ("API") 180, described in more detail below, and also interfaces with the ultrasound system 100 via the external interface 175. The configuration/control application 150 is a custom designed software application which operates on the PDA 140 and is designed to interface, through the external interface 175 and PDA interface 130, with the processor 120 of the ultrasound system 100, either directly or via the user interface 135, for the purpose of controlling and exchanging data with the ultrasound system, as will be described.

When the PDA 140 is docked with the ultrasound system 100 via the PDA interface 130 and external interface 175, the configuration/control application 150 is capable of exchanging data with and controlling the ultrasound system 100. As used herein, the term "docked" is defined to mean that the PDA 140 is externally coupled with the ultrasound system 100 via the external interface 175 and PDA interface 130, utilizing one or more of the interface technologies described above, to effect a logical link such that data interchange is possible between these devices, i.e. any necessary protocol negotiation has been completed and each device logically/programmatically "recognizes" the presence of the other device. Docking may occur when the PDA 140 is placed in a cradle (i.e. a device designed to receive the PDA 140 and make a connection with the external interface 175) connected to the PDA interface 130 or may occur when the PDA 140 is brought within a particular proximity of the PDA interface 130. In one embodiment, the PDA 140 is permanently docked with the PDA Interface 130 no matter where the PDA 140 is located, such as via wireless connection. In an alternate embodiment, more than one PDA 140 may be docked with the PDA interface 130 and/or one PDA 140 may dock with more the PDA interface 130 of more than one ultrasound system 100. Where more than one PDA 140 is docked with a system 100, the interface 130 is capable of resolving conflicts among the docked PDA's 140. Such conflicts may be resolved by locking out one or more of the PDA's 140 from being able to control the ultrasound system 100, or by mediating the access among the docked PDA's 140 such as through a round robin or other priority scheme. In one embodiment, the PDA 140 and configuration/control application 150 are capable of performing any command or control function on the system 100 as can be done via the user interface 135 of the system 100, such as setting operational parameters. In an alternate embodiment, the PDA 140 and configuration/control application 150 are capable of performing a subset of the functions available via the user interface 135 of the system 100.

When docked, the configuration/control application 150, via the user interface 145 of the PDA 140, permits a user to remotely control the ultrasound system 100 via the PDA 140 alone, or in combination with the user interface 135 of the system 100 itself. The PDA 140 provides for display of system responses, indicators and operational displays. As described above, in one embodiment, the PDA 140 is capable of displaying the images generated by the system 100. In an alternate embodiment the PDA 140 is capable of completely supplanting the user interface 135 thereby allowing the bulk of the ultrasound system 100 to be concealed or otherwise unobtrusively located such that access to the user interface 135 is difficult or impossible.

Via the remote control capability, the configuration/control application 150 further permits a user of the PDA 140 to perform basic or complex maintenance operations on the ultrasound system 100. Such maintenance operations include performing calibrations, adding or removing components, both hardware and software, and managing software licenses. It will be appreciated that the configuration/control application 150 may include macro functions or other automated components which permit simplified implementation of complex or multi-part operations.

As was described above, the PDA 140 further includes PIM software applications 155. The PIM software applications 155 may be custom designed for use in the ultrasound/clinical setting or may be standard, off-the-shelf applications which are utilized and/or customized for use in the ultrasound/clinical setting. For example, the calendar/scheduling PIM application 155 may be custom designed to provide data fields appropriate for scheduling examinations, such as for the examination type or medical insurance data. Alternately, the standard calendar/scheduling PIM application 155 may be used wherein standard fields, such as the description field, are used to record the examination specific data.

In the clinical setting, the calendar/scheduling PIM application 155 may be used for patient scheduling, staff scheduling, equipment utilization/scheduling, maintenance scheduling, software license expiration/maintenance or any other temporally based or categorized data. The contacts management PIM application 155 may be used for maintaining staff, patient, reference, support, supplier, and/or other contact information. The notes PIM application 155 may be used to record typed, handwritten or audio examination notations or reports. The PIM applications 155 may further include an electronic document viewer such as a PDF file viewer or electronic book viewer which allows the clinician to load and view reference materials such as a pharmaceutical reference manual.

The PIM software applications 155 may be counterparts to centralized full featured applications running on a central server or network to which the PIM software applications 155 are synchronized when the PDA 140 is docked with the central server. For example, a clinic may maintain a central computing system for scheduling patients and storing patient history and examination result data files. One or more docking stations may be provided throughout the clinic to which a user may dock their PDA 140 to synchronize the data stored in their PDA 140 with that stored on the central server. For example, a clinician may dock their PDA 140 to synchronize their scheduling application thereby updating the patient schedule for the day or and changes thereto.

Data transfer and/or communications applications may also be provided. For example, an email application may be provided which permits receipt and transmission of electronic messages/mail via the external interface 175. Such an application may be used to transmit examination results/reports or receive patient scheduling or contact information changes.

In addition to the PIM applications 155, custom application software 185 may be loaded on the PDA 140. Such custom software may include examination report generators, software license management and examination data transfer applications. These custom applications 185 may also have synchronization capabilities with a centralized server or computer network. Where the PDA 140 includes an optical reader 160, as described above, custom application software 185 may be provided to allow a user to input data into any of the other PIM applications 155 or the configuration control application 150 using the optical reader to scan visual data representations such as barcodes. For example, where a technician wishes to use a new transducer probe with the ultrasound system 100, the system 100 may need to have certain operational parameters configured to properly utilize the new probe. These operational parameters values may be encoded as barcodes imprinted on the transducer probe housing. The technician can then use the optical reader 160 to scan the barcodes thereby inputting the operational parameter values into the system 100 via the configuration/control application 155. This is much less expensive than implementing an automated "plug an play" architecture between the ultrasound probe or other optional component and the system 100. In one embodiment, the barcodes can include commands as well as data, allowing the user to simply scan the barcodes to accomplish tasks without enabling or otherwise configuring an application or the PDA 140 or system 100 to receive the scanned barcodes.

Other applications using barcodes include software licensing and maintenance. Software programs are typically protected to prevent unauthorized use or duplication by requiring that the user possesses a license key. The license key is typically an encoded alphanumeric string which the user must enter into the software program in order to enable its operation. These alphanumeric strings are typically very long and complex and usually contain error and tamper detection codes. Using the optical reader, a software company may distribute the license key values as barcodes allowing the user to easily scan them to enable the software. Further, using barcodes would allow a manufacturer to distribute the license keys via facsimile or other visual distribution technology.

For maintenance operations, such operations can be set out as a sequence of one or more barcodes which encode the maintenance operations. Such sequences may then be discretely placed on or near the ultrasound system 100 where a user can easily find them and scan the barcodes to perform the requisite maintenance operation. Further, maintenance manuals may include bar codes along with descriptions of the maintenance operations. A technician performing a maintenance operation therefore need only scan the appropriate barcodes as they read through the manual to cause or indicate performance of the maintenance or to obtain further stored information related to the maintenance.

Further, the clinician operating the ultrasound machine may use bar-coded checklists or other documents, such as a patient chart, to configure and set up the system 100. Such barcodes can eliminate the need to perform complex configuration operations to set up the system 100 for a particular exam.

The use of pre-defined barcodes to enable operations or configure the system 100 eliminates the need for the operator to have detailed system-specific knowledge, eliminates human error and ensures that the desired operational performance is achieved. In situations, where patient throughput is important, such efficiencies can reduce the transition time for the examination room from patient to patient allowing shorter intervals between examination appointments. Further, barcodes facilitate easy and error free dissemination of complex information. Such information, encoded as barcodes, may be shared among users via facsimile or photocopy and even scanned into a computer as an image and shared via electronic mail.

The PDA 140 operating system further provides for integration and synchronization of the PIM 155 and other applications, allowing them to share data among themselves, with a central computer system, as described above, and with the ultrasound system 100. For example, a calendar entry scheduling a particular patient for an exam may be linked with the contact entry for that patient so that the clinician can easily retrieve the patient's telephone number. In addition, the scheduling PIM application 155 is synchronized with a counterpart scheduling application located in the ultrasound system 100 or other computer to which the PDA 140 is docked. In this way, a central scheduling system may be maintained whereby the clinician docks their PDA 140 with the scheduling system to synchronize and obtain the latest patient schedule.

As described above, the configuration/control application 150 provides an API 180 which allows the integration of the functionality of the PIM applications 155 and other custom applications 185 loaded on the PDA 140 with the ultrasound system 100. In this way, the PIM applications 155 and custom applications 185 can control the function of the ultrasound system 100 and/or exchange data with the ultrasound system 100. For example, where the scheduling application 155 has an examination appointment scheduled/stored for a particular patient, configuration parameters regarding the examination type and other pertinent information may be stored with the appointment. At the time of the appointment, or at a predefined time period prior to the appointment, once the PDA 140 is docked with the ultrasound system 100, the scheduling application 155 can send the configuration parameters or identifiers for the examination to the ultrasound system 100 via the configuration/control application 150 and API 180 automatically configuring the system 100 for the examination to be given. During the examination, the technician may need to change some of the configuration parameters. This may be done via the user interface 135 on the ultrasound system 100 or via the user interface 145 on the PDA 140 via the configuration/control application 150. Further, any changed settings can be stored in the scheduling application, or in a custom application, as patient history data and used again to configure the system 100 during future examinations or for review with resulting diagnostic information. In alternative embodiments, the scheduling application 155 can refer to the stored patient history data to determine how to configure the ultrasound system 100 for the current examination. The patient history data contains information such as past examination type, past configuration settings or past examination results.

In one embodiment, the ultrasound system 100 includes customizable preference settings which can be configured by the user of the system 100. Such preference settings may include display brightness, display colors, font size, imaging mode, filter settings, processor settings, depth gain settings, frequency selections, and other user interface or system 100 operational preferential parameters. Particular settings for these parameters may be stored on a PDA 140 associated with a particular user. In this setting, each use of the system 100 may have their own PDA 140 and may configure the stored preferential settings to their own preferences. When the PDA 140 is docked with the ultrasound system 100, the PDA 1040, via the configuration/control application 150 automatically configures the system 100 to use the preferential parameters stored in the PDA 140. In this way, the PDA 140 acts as a personality module, automatically customizing the ultrasound system 100 to the clinicians preferences. In one embodiment, the preference values are stored in the configuration/control application 150. In an alternate embodiment, a separate custom application 185 maintains the preference values and interfaces with the API 180 of the configuration/control application 150 as described above. When the PDA 140 is undocked from the system 100, the settings can be returned to their default values or left in their current state until another clinician docks their PDA 140 with other settings.

Further, preference information stored on the PDA 140 may include software license keys for enabling software operation on the ultrasound system 100 or enabling different levels of access to the hardware or software of the ultrasound system 100. In this way, when the PDA 140 is docked with the system 100, the license keys are passed to the system 100 to enable the software or authorize a particular access level. When the PDA 140 is undocked, the software or access level is disabled. This permits the individual distribution of software licenses or authorization of access without requiring the user to remember and provide passwords or other manual authentication.

Other applications may use the API 180 to exchange examination data with the ultrasound system 100. For example, a report generating application operating on the PDA 140 may retrieve examination results from the system 100 via the configuration/control interface 150 for automated incorporation into an examination report. Further, as described, the report generating application may further interface with the scheduling and contacts applications 155 to retrieve the patient's personal information and appointment data.

Figure 2:
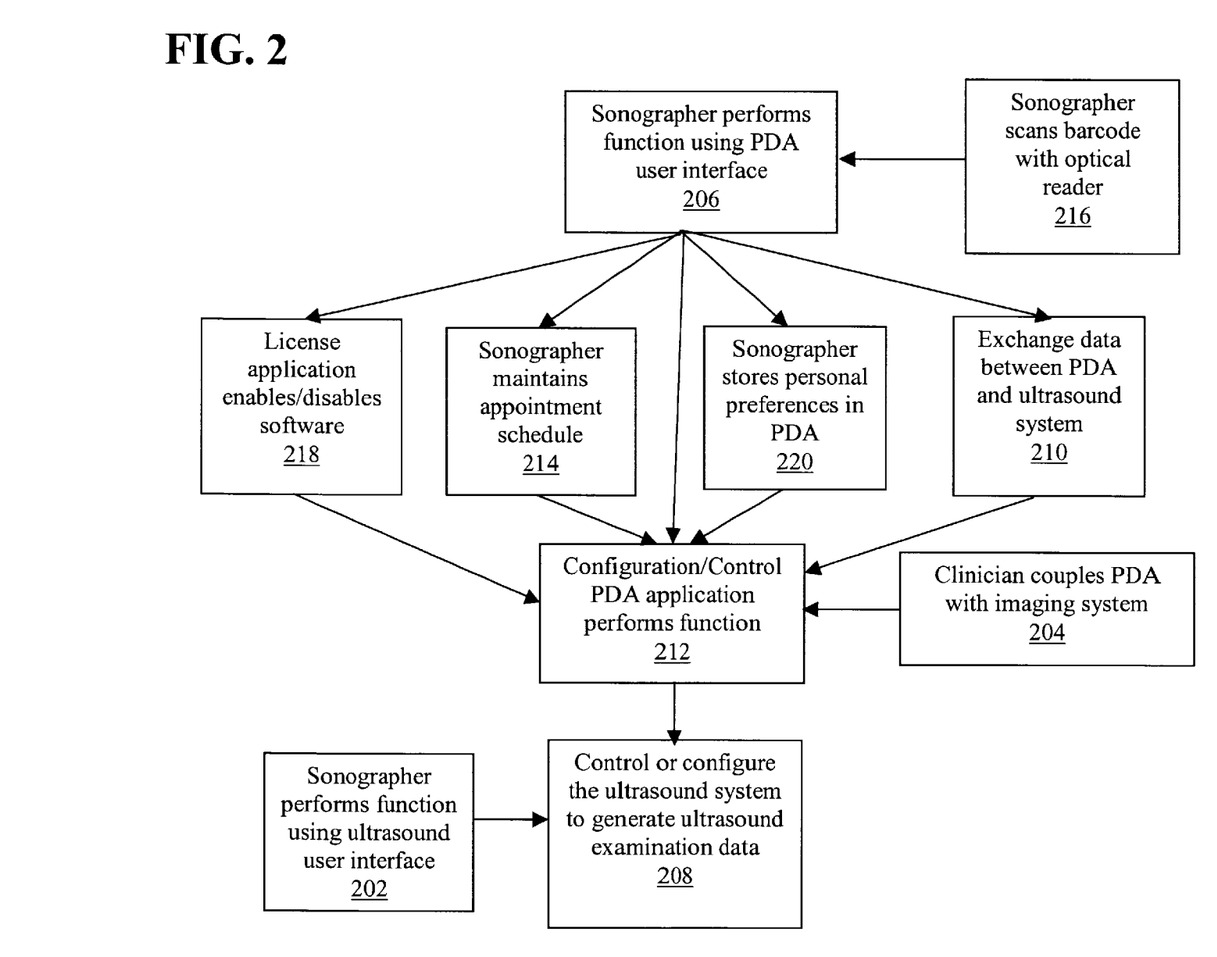
FIG. 2 depicts a flow chart showing exemplary operation of the system of FIG. 1.

Basic operation of the ultrasound system 100 utilizing the PDA 140 is shown in FIG. 2. The sonographer controls the ultrasound system 100, such as the transmit and receive beamformers 110, 115 or the processor 120, via the ultrasound system's user interface 135 (Blocks 202, 208). This is the normal operating procedure for using the system 100. Alternately, the sonographer may couple/dock a PDA 140 with the system 100 and control the ultrasound system 100 or exchange data between the ultrasound system 100 and the PDA 140 via the PDA user interface 145 (Blocks 204, 206, 212). As described, the PDA user interface 145 may provide full control over all functions of the system 100 or just a subset of the functions. In utilizing the PDA user interface 145, the sonographer may utilize the optical reader 160, if present, to input data by scanning visual representations such as bar codes or alphanumeric codes (block 216). The sonographer's interactions with the PDA user interface 145 cause the configuration/control application 150 to interface with the system 100 and perform the requisite functions.

The sonographer may also use the PDA user interface 145 to interact with other functions of the PDA 140 such as a license manager application, a scheduling application, a personal preference application and a data interchange application (blocks 218, 214, 220, 210). These applications are described in more detail elsewhere in the specification. Each these applications may interface with the configuration/control application 150 to automate configuration and control functions as described.

The disclosed embodiments further support exemplary operation as follows. A patient calls in or is referred to an imaging clinic. A receptionist, at a central computer station or utilizing a PDA 140, determines if the patient is a new or existing patient and starts a new file or retrieves an existing file accordingly. This determination may be made by accessing a central patient database and attempting to retrieve a patient history electronic file. If no file exists, the receptionist may create one. The patient then schedules an examination and the receptionist logs this appointment into a scheduling application, such as a centralized schedule management system. The appointment data includes the nature of the examination and any pertinent examination history for that patient, or electronic links thereto.

On the day of the patient's appointment, or in advance, the patient is assigned to a particular sonographer or to a particular examination room or ultrasound machine. The sonographer's preferably each have their own PDA 140 as described above. Occasionally, each sonographer docks their PDA 140 with the central scheduling application and synchronizes their PDA's 140 scheduling application. During this synchronization, the scheduling application on the assigned sonographer's PDA 140 is loaded with the appointment. Alternately, the PDA 140 may automatically wirelessly dock with the central scheduling system or central patient database.

When the patient arrives, they are shown to the appropriate examination room by the assigned sonographer or other staff member. The assigned sonographer is aware of the appointment via a reminder generated on their PDA 140 by the scheduling application. If the patient is not present, the sonographer may access the contacts function of the PDA 140 to determine the patient's phone number to see if they are coming or not. The contacts function is linked with the scheduling application such that the sonographer can access the contact information directly from the scheduling application.

Once the patient is in the examination room, or prior, the sonographer docks their PDA 140 to the ultrasound system 100. The PDA 140 immediately, or at a scheduled time, configures the ultrasound system 100 to the preferences of the sonographer and enables any software or access levels that the sonographer is authorized to have access to. Further, the exam type and examination history information is analyzed and the proper configuration settings, based on this information, are set up on the ultrasound system 100. Such settings may be determined based on past examination results, past examination type or the specified type of examination to be performed during the present appointment. Once configured, the PDA 140 user interface displays the remote control and remote image display of the ultrasound system 100. The sonographer then performs the examination utilizing the ultrasound system 100. During the examination, the sonographer may input into the PDA 140, or the ultrasound system 100, any written, typed or audio notations and annotations to the examination results.

If, during or prior to the examination, it is determined that a different ultrasound probe is needed (as determined and indicated by the PDA 140 based on the exam type or manually by the sonographer), the sonographer retrieves and connects the new transducer. The sonographer then scans the barcodes imprinted on the transducer housing using the optical reader 160 of the PDA 140. The scanned barcodes automatically command the configuration/control application 150 to properly configure the ultrasound system 100 to utilize the new transducer.

During the examination, the sonographer may consult reference documents stored on the PDA 140. Further, if a consultation is required, the sonographer may access the contacts function via the scheduling function to determine the telephone or other contact information of the primary care physician or radiologist. If the PDA 140 is so equipped, the sonographer may call or send an email to the primary care physician or radiologist.

Once the exam is complete, the sonographer accesses the report generation application on the PDA 140 which automatically downloads the examination results and stored images and associates them with any notations or annotations created by the sonographer during the exam. The sonographer may edit or otherwise add to the report. In one embodiment, an electronic signature function is provided enabling the sonographer to sign off on the report electronically.

The patient is then shown out of the examination room and the sonographer undocks their PDA resetting all of the configuration settings, software licenses and access levels of the ultrasound system 100. The sonographer may then dock their PDA 140 with a central computer system to download the exam results and/or report. This also updates the patient's history file. The downloaded results and/or report may then be transmitted, electronically or via other means, to the patient's primary care physician or radiologist.

Further, the sonographer may stop at a display station such as review docking station where they can dock their PDA's 140 to view or discuss with colleagues, the exam results or reports on a large external monitor.

In an alternate embodiment, the PDA 140 has wireless capability and the capability of being docked wirelessly with more than one remote device. In this embodiment, data such as scheduling information is constantly being updated to the PDA 140. Further, in this embodiment, the PDA 140 only docks with an ultrasound system 100 when it is within a certain proximity of the system 100 or when manually instructed to do so by the user. Once docked, operation is as discussed above.

Further, the PDA 140 may also instruct the user to perform maintenance tasks, either according to a maintenance schedule or as needed. In this case, the PDA 140 may provide step by step instructions to perform the task or the PDA 140 may perform the task automatically. Where user input is required, the user may use the optical reader 160 to scan in configuration parameters or maintenance commands.

The scheduling capabilities of the PDA 140 may also be used for allocating staff and equipment resources, scheduling vacations and office holidays and managing the distribution of the appointment load among the available staff.

In this way, the functionality of a PDA 140 is used to enhance the functionality of the ultrasound system 100 with the benefits being simpler, more efficient and accurate utilization of the system 100. This results in lower costs and higher patient throughput while maintaining safe and accurate diagnosis.

It will be appreciated that the optical reader may be part of the ultrasound system 100 capable of being used with or without a PDA 140. Without the PDA 140, the optical reader interfaces with the user interface 135 of the ultrasound system 100 to permit the functionality described above for configuring and controlling the system 100 via visual data representations such as bar codes. Any of the various information discussed above or sub-sets thereof may reside in any of the computer network, PDA or ultrasound system for transfer to or control of another of the network, PDA or ultrasound system.

It is therefore intended that the foregoing detailed description be regarded as illustrative rather than limiting, and that it be understood that it is the following claims, including all equivalents, that are intended to define the spirit and scope of this invention.

We claim:

1. A medical diagnostic imaging system for use with a personal digital assistant, said medical diagnostic imaging system comprising:
   a transmitter;
   a receiver;
   a transducer coupled with said transmitter and receiver;
   a processor coupled with said transmitter and receiver and operative to control said transmitter and receiver and generate medical diagnostic imaging data representative of the operation thereof,
   a first user interface coupled with said processor and operative to allow a user to perform at least one of a first set of control functions on said imaging system; and
   a personal digital assistant ("PDA") interface coupled with said processor and operative to externally couple a PDA with said imaging system, said PDA comprising a second user interface operative to allow a user to perform at least one of a second set of control functions on said imaging system, said PDA interface being further operative to receive input data from said PDA and transmit output data to said PDA.

2. The system of claim 1, wherein said second set of control functions comprises a subset of said first set of control functions.

3. The system of claim 1, wherein said input data comprises at least one command to control said at least one of said second set of control functions.

4. The system of claim 3, wherein said output data represents a response to said at least one command, wherein said second user interface is further operative to display said response.

5. The system of claim 3, wherein said at least one command is generated by a configuration application operating on said PDA and operative to generate said at least one command to configure operation of said imaging system.

6. The system of claim 5, wherein said configuration application is coupled with a scheduling application operating on said PDA, said scheduling application operative to maintain an examination schedule, said configuration application operative to configure said imaging system based on said examination schedule.

7. The system of claim 6, wherein said configuration application generates said command to configure said imaging system based on a type of examination to be performed.

8. The system of claim 6, wherein said configuration application generates said command to configure said imaging system based on an examination history of a scheduled patient.

9. The system of claim 8, wherein said examination history comprises at least one of results of a past examination, type of past examination and configuration settings of said imaging system utilized in a past examination.

10. The system of claim 5, wherein said configuration application is further operative to generate said at least one command to perform maintenance on said imaging system.

11. The system of claim 5, wherein said command comprises a license to enable a software program to operate on said imaging system.

12. The system of claim 5, wherein said command comprises an authorization to enable an access level to a software program operating on said imaging system.

13. The system of claim 5, wherein said command comprises a personal preference for at least one said second set of control functions, said preference being personal to an owner of said PDA.

14. The system of claim 1 wherein said second user interface comprises an optical reader operative to input data into said PDA, said data being visually represented on a medium.

15. The system of claim 14, wherein said optical reader comprises a bar code reader, said data being visually represented on said medium using a bar code.

16. The system of claim 14, wherein said medium comprises an optional component of said imaging system, said data representing configuration data to enable use of said optional component with said imaging system.

17. The system of claim 14, wherein said data represents at least one configuration parameter for configuring said imaging system.

18. The system of claim 17, wherein said medium comprises a checklist for said at least one configuration parameter.

19. The system of claim 1, wherein said PDA interface comprises a cradle to which said PDA is capable of being docked.

20. The system of claim 1, wherein said PDA interface comprises a wireless interface.

21. The system of claim 1, wherein said PDA interface comprises a network interface.

22. The system of claim 1, wherein said PDA interface is further operative to disable said first user interface when said PDA is coupled with said imaging system.

23. The system of claim 22, wherein said first user interface is removable.

24. A method of using a personal digital assistant with a medical diagnostic imaging system, said system comprising a processor, a first user interface coupled with said processor and a personal digital assistant ("PDA") interface coupled with said processor, said method comprising:
   (a) controlling said imaging system and generating medical ultrasound imaging data representative of the operation thereof;
   (b) performing at least one of a first set of control functions on said imaging system via said first user interface;
   (c) coupling, externally, a PDA with said imaging system via a personal digital assistant ("PDA") interface coupled with said first user interface and said processor, said PDA comprising a second user interface;
   (d) performing at least one of a second set of control functions on said imaging system via said second user interface;
   (e) receiving input data by said PDA interface from said PDA; and
   (f) transmitting output data by said PDA interface to said PDA.

25. The method of claim 24, further comprising:
   (g) limiting said second set of control functions to a subset of said first set of control functions.

26. The method of claim 24, wherein said input data comprises at least one command to control said at least one of said second set of control functions, said method further comprising:
   (g) generating said at least one command, by a configuration application operating on said PDA, to configure operation of said imaging system.

27. The method of claim 26, wherein said output data comprises at least one response to said at least one command, said method further comprising:

(h) displaying said at least one response by said second user interface on said PDA.

28. The method of claim 26, wherein said configuration application is coupled with a scheduling application operating on said PDA, said method further comprising:
(h) maintaining an examination schedule by said scheduling application; and
(i) configuring, by said configuration application, said imaging system based on said examination schedule.

29. The method of claim 28, further comprising:
(j) generating, by said configuration application, said command to configure said imaging system based on a type of examination to be performed, said type of examination being stored in said examination schedule.

30. The method of claim 28, further comprising:
(j) generating, by said configuration application, said command to configure said imaging system based on an examination history of a scheduled patient, said examination history being coupled with said examination schedule.

31. The method of claim 30, further comprising
(k) storing in said examination history at least one of results of a past examination, type of past examination and configuration settings of said imaging system utilized in a past examination.

32. The method of claim 26, further comprising:
(h) generating, by said configuration application, said at least one command to perform maintenance on said imaging system.

33. The method of claim 26, wherein (g) further comprises providing a license for enabling a software program to operate on said imaging system.

34. The method of claim 33, further comprising:
(h) enabling said software when said PDA is coupled with said PDA interface;
(i) disabling said software when said PDA is decoupled from said PDA interface.

35. The method of claim 26, wherein (g) further comprises authorizing user access to an access level of a software program operating on said imaging system.

36. The method of claim 35, further comprising:
(h) authorizing said user access when said PDA is coupled with said PDA interface; and
(i) revoking authorization of said user access when said PDA is decoupled from said PDA interface.

37. The method of claim 26, wherein (g) further comprises configuring at least one parameter of said imaging system according to a personal preference for at least one said second set of control functions, said preference being personal to an owner of said PDA.

38. The method of claim 24, further comprising:
(g) scanning data optically into said second user interface of said PDA, said data being visually represented on a medium.

39. The method of claim 38, wherein (g) further comprises scanning a bar code affixed to a medium, said bar code visually representing said data.

40. The method of claim 38, wherein said medium comprises an optional component of said imaging system, said method further comprising:
(h) configuring use of said optional component with said imaging system by said scanning.

41. The method of claim 38, wherein said data represents at least one configuration parameter for configuring said imaging system.

42. The method of claim 41, wherein said medium comprises a checklist for said at least one configuration parameter.

43. The method of claim 24, further comprising:
(g) disabling said first user interface when said PDA is coupled with said imaging system.

44. A medical diagnostic imaging system for use with a personal digital assistant, said medical diagnostic imaging system comprising:
processing means for generating medical diagnostic image data using a transducer coupled with transmit and receive means;
a first user interface means for allowing a user to perform at least one of a first set of control functions on said imaging system, said first set of control functions comprising at least controlling said processing means; and
a personal digital assistant ("PDA") interface means coupled with said first user interface means for externally coupling a PDA with said imaging system, said PDA comprising a second user interface means for allowing a user to perform at least one of a second set of control functions on said imaging system, said PDA interface means being further operative to receive input data from said PDA and transmit output data to said PDA.

45. In a medical diagnostic imaging system, an improvement for operating the imaging system, the improvement comprising:
a personal digital assistant interface connected with the system; and
a processor of the system operative to allow a personal digital assistant to control the system via the personal digital assistant interface.

46. A medical imaging system for use with a personal digital assistant, said medical imaging system comprising:
a beamformer;
a processor coupled with said beamformer and operative to control said beamformer and generate medical imaging data representative of the operation thereof;
a first user interface coupled with said processor and operative to allow a user to perform at least one of a first set of control functions on said imaging system; and
wherein said first user interface further comprises an optical reader operative to input data into said first user interface, said data being visually represented on a medium, said data operative to perform at least one of a second set of control functions on said imaging system.

47. The system of claim 46, wherein said optical reader comprises a bar code reader, said data being visually represented on said medium using a bar code.

48. The system of claim 47, wherein said data as visually represented is capable of being transferred by at least one of facsimile, electronic mail, and postal mail.

49. The system of claim 47, wherein said medium comprises an optional component of said imaging system, said data representing configuration data to enable use of said optional component with said imaging system.

50. The system of claim 47, wherein said data represents at least one configuration parameter for configuring said imaging system.

51. The system of claim 50, wherein said medium comprises a checklist for said at least one configuration parameter.

52. A medical imaging system for use with an external interface, said medical imaging system comprising:

a transmitter;

a receiver;

a transducer coupled with said transmitter and receiver;

a processor coupled with said transmitter and receiver and operative to control said transmitter and receiver and generate medical imaging data representative of the operation thereof;

a first user interface coupled with said processor and operative to allow a user to perform at least one of a first set of control functions on said imaging system; and a second user interface coupled with said first user interface and said processor and operative to externally wirelessly couple an electromagnetic spectrum data source with said imaging system, said second user interface being operative to allow a user to perform at least one of said first set of control functions on said imaging system.

53. The system of claim 52, wherein:

the second user interface further comprises one of a barcode scanner and a personal digital assistant interface.

54. The method of claim 53, wherein said electromagnetic spectrum data source comprises a personal digital assistant.

55. The method of claim 53, wherein said electromagnetic spectrum data source comprises a bar code.

56. The system of claim 52, wherein said electromagnetic spectrum data source operates in the infrared spectrum.

57. The system of claim 52, wherein said electromagnetic spectrum data source operates in the RF spectrum.

58. The system of claim 52, wherein said electromagnetic spectrum data source operates in the visual spectrum.

* * * * *

UNITED STATES PATENT AND TRADEMARK OFFICE
CERTIFICATE OF CORRECTION

PATENT NO. : 6,475,146 B1
DATED : November 5, 2002
INVENTOR(S) : Freiburger et al.

It is certified that error appears in the above-identified patent and that said Letters Patent is hereby corrected as shown below:

<u>Title page,</u>
Item [75], Inventors, "Frelburger" and substitute -- Freiburger -- in its place.

Signed and Sealed this

First Day of June, 2004

JON W. DUDAS
*Acting Director of the United States Patent and Trademark Office*